(12) United States Patent
Karge et al.

(10) Patent No.: US 6,233,773 B1
(45) Date of Patent: *May 22, 2001

(54) COMBINATION MOTORIZED TOOTHBRUSH AND PLAQUE REMOVAL DEVICE

(76) Inventors: Hans J. Karge, 8540 S. Sepulveda Blvd., #1200, Los Angeles, CA (US) 90045; Robert C. Wood, 1441 Huntington Dr., #304, South Pasadena, CA (US) 91030

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/138,083

(22) Filed: Aug. 21, 1998

Related U.S. Application Data

(63) Continuation of application No. 08/997,410, filed on Dec. 23, 1997, now abandoned.

(51) Int. Cl.[7] .................................................. A46B 13/04
(52) U.S. Cl. ................................................. 15/29; 601/165
(58) Field of Search ........................... 15/24, 29; 601/162, 601/163, 165; 433/216

(56) References Cited

U.S. PATENT DOCUMENTS

| | | | | |
|---|---|---|---|---|
| 3,927,434 | * | 12/1975 | Burgess | 15/24 |
| 3,968,789 | * | 7/1976 | Simoncini | 15/29 |
| 4,619,009 | * | 10/1986 | Rosenstater | 15/29 |
| 4,783,871 | * | 11/1988 | Rich, Jr. | 15/24 |
| 4,903,688 | * | 2/1990 | Bibby | 433/216 |
| 5,142,723 | * | 9/1992 | Lustig | 15/22.1 |
| 5,145,369 | * | 9/1992 | Lustig . | |
| 5,208,933 | | 5/1993 | Lustig et al. . | |
| 5,544,382 | * | 8/1996 | Giuliani | 15/22.1 |
| 5,573,398 | * | 11/1996 | Towle | 15/24 |
| 5,700,146 | * | 12/1997 | Kucar | 601/162 |

FOREIGN PATENT DOCUMENTS

| | | | | |
|---|---|---|---|---|
| 2735427 | * | 2/1979 | (DE) | 433/216 |
| 3631770 | * | 3/1988 | (DE) | 15/24 |

* cited by examiner

*Primary Examiner*—Randall E. Chin
(74) *Attorney, Agent, or Firm*—Christie, Parker & Hale, LLP

(57) ABSTRACT

A combination motorized toothbrush and gum cleaning device which uniquely incorporates the best features of a motorized toothbrush and a pressurized fluid stream cleaning gum-cleaning system. A pump assembly and power source are housed in a plastic housing and a flexible hose leads from the pump to a hollow brush handle which contains a D.C. motor, a gear train terminating in an oscillating shaft and a pair of switches. A removable and replacable brush head assembly plugs onto the top of the brush head and the oscillating shaft causes the bristles of the brush head to oscillate. A hollow tube portion also is incorporated into the brush head assembly which delivers a high power stream of water or other fluid out the center of the brush head and can be directed towards the users gum line and between the users teeth.

10 Claims, 4 Drawing Sheets

COMBINATION MOTORIZED TOOTHBRUSH AND PLAQUE REMOVAL DEVICE

This is a continuation application of application Ser. No. 08/997,410 filed Dec. 23, 1997, now abandoned.

BACKGROUND OF THE INVENTION

Devices for the cleaning of teeth and the care of gums have been in existence for many years. Toothbrushes employing a powered means to cause the bristles of the brush to move, have been in existence for the last twenty-five years. This feature allows the user to have access to many more brush strokes within a given brush period thereby increasing the effectiveness of the brushing practice. Since then numerous powered toothbrushes have been introduced into the market place, each having either a reciprocal, rotational or oscillating motion of the bristles.

In addition to brushing the teeth, it has been found that cleaning under the gums also helps prevent tooth decay and gum disease. A device which has proven effective in cleaning under gums and which has been on the market for the last twenty years is called the "Water Pik" manufactured by Teledyne. This device shoots a strong fine stream of water into the user's mouth and is aimed at the gum line. The water cleans out debris from under the gums and around the teeth. While both the powered toothbrush and the Water Pik do their jobs effectively, it is necessary for a person to purchase two products and to have two products taking up space on a bathroom counter top, or, when traveling, it is necessary to carry two devices in ones traveling case. This situation puts strain on a household's financial budget, causes a cluttered look on the bathroom counter top and causes extra weight and bulk while traveling.

OBJECTS AND SUMMARY OF THE PRESENT INVENTION

It is an object of the present invention to solve the above stated problems by providing a unique tooth and gum cleaning device which combines the motorized motion of a powered toothbrush with a gum cleaning, powered stream of liquid such as water for use into one device. By uniquely combining the two devices one can produce a single device that is smaller and less costly than existing single use devices.

The present invention uniquely combines the two devices by providing a brush handle having within it a reciprocating gear train powered by a small D.C. motor and a water line which receives water via a hose from a separate pump and reservoir assembly. The gear train terminates in an oscillating shaft and the water line terminates in a female receptacle located to one side of the oscillating shaft. A removable and replacable brush head assembly has two longitudinal chambers located in a hollow neck. One chamber receives the oscillating shaft and the second chamber terminates in a male plug which fits into the water receptacle located at the top of the brush handle. A flexible, hollow hose stretches between the base unit containing the pump and water reservoir and the bottom of the toothbrush handle. The hose carries water or other fluid as well as two pairs of sheathed wires, one of pair of which carries electrical current to the D.C. motor, the other pair of which attaches to a switch located in the handle for turning on and off the water pump. When the pump is activated, water progresses up the brush handle into the neck of the brush head and then is transported at a ninety degree angle, through the center of the oscillating brush head so that a powered stream of water can be emitted from the brush head when the user presses the momentary switch located in the brush handle. Because the water outlet is at the very center of the rotatably reciprocating brush head it remains stationary even when the brush head is being activated.

The entire unit can be stored in an upright position so that a minimum of counter space is occupied when the unit is not in use. Additional features include an audio chip telling the user how much time is left to brush each quadrant of the mouth, a timer to check on length brushing time. A place for storing an extra brush head and a provision for hidden hose storage.

DETAILED DESCRIPTION OF THE DRAWINGS

Figure 1:
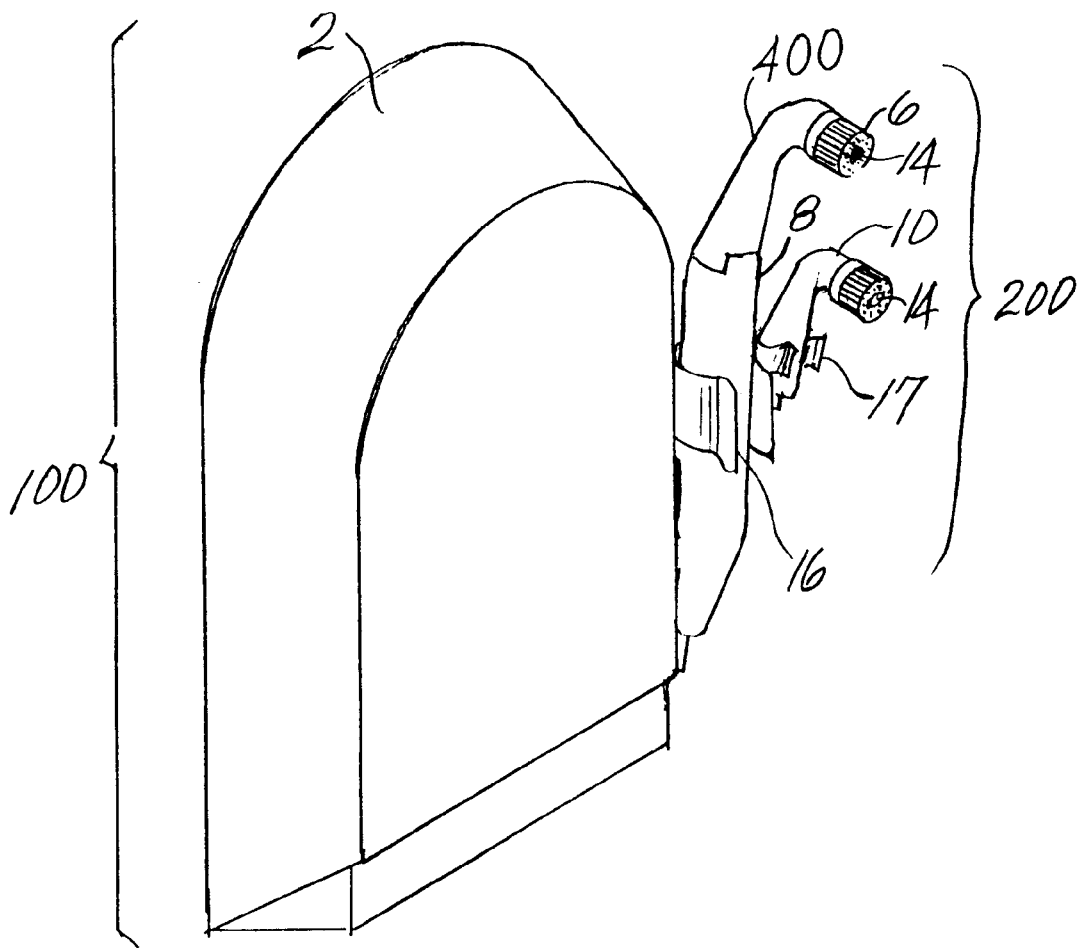
FIG. 1 is a perspective view of the present invention in the storage position.
Figure 2:
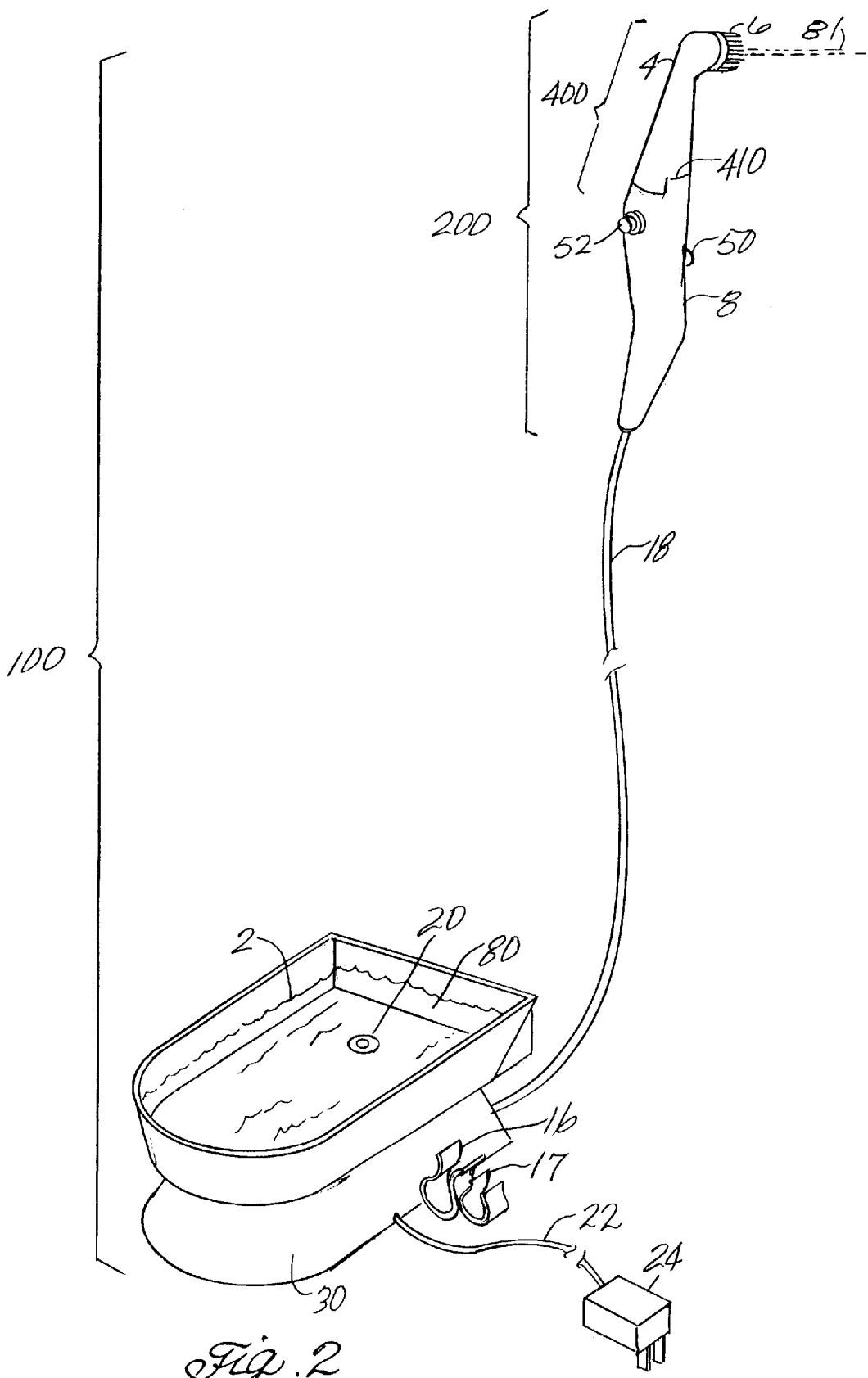
FIG. 2 is a perspective view of the present invention in the use position.
Figure 3:
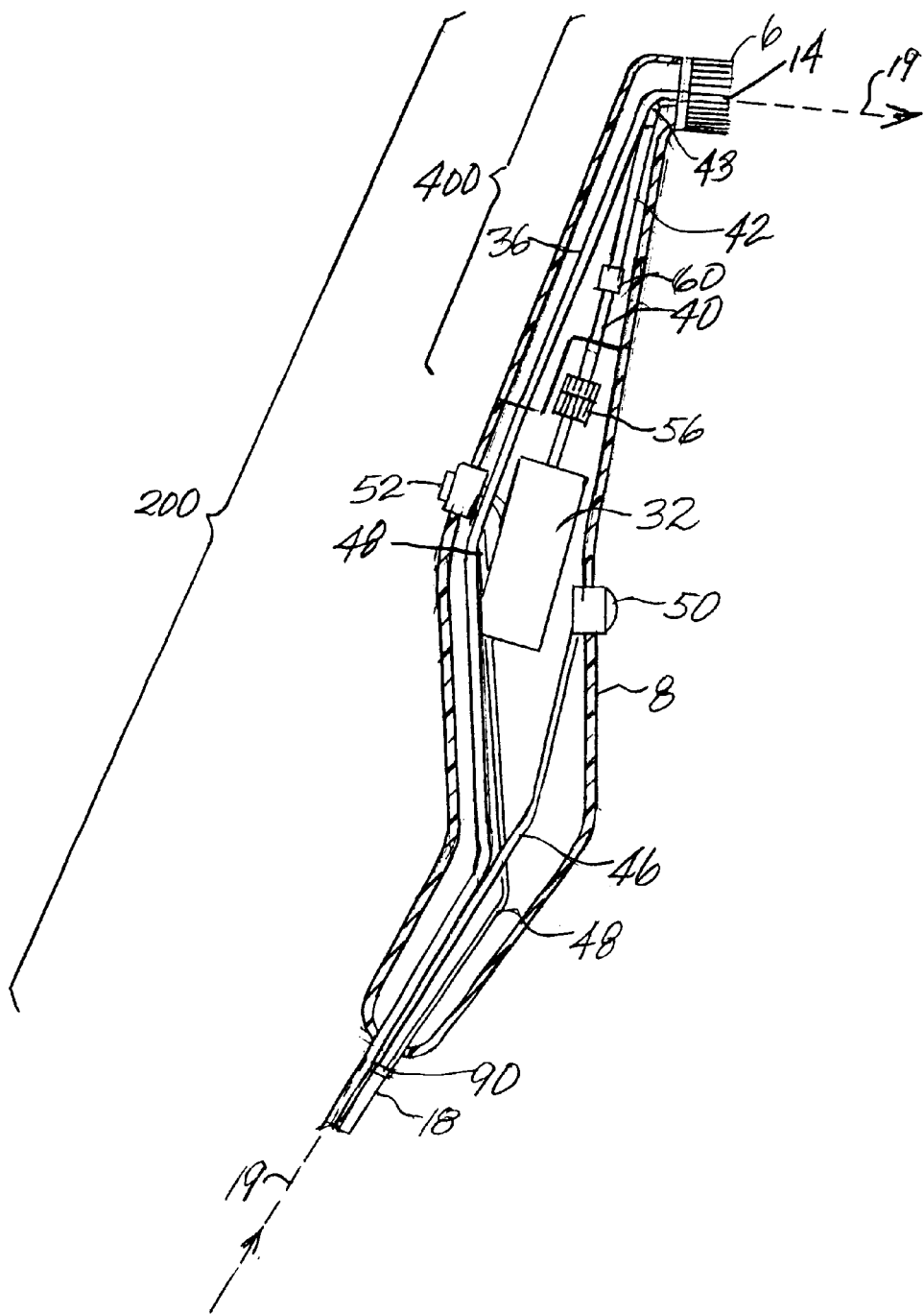
FIG. 3 is a side section view of the tooth brush and water delivery portion of the present invention.
Figure 4:
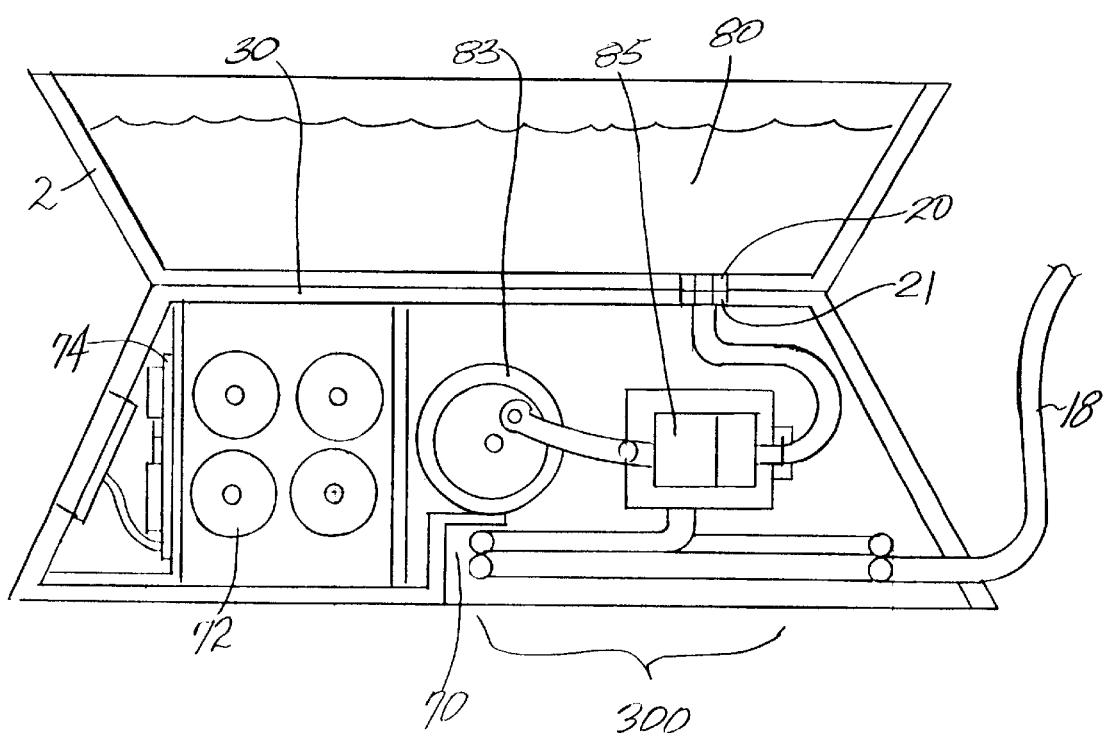
FIG. 4 is a side section view of the pump housing and water reservoir portion of the present invention.

Referring now to FIG. 1 we see the combination motorized toothbrush and gum cleaning device of the present invention 100 in its storage position. Water reservoir 2 is standing in a vertical orientation so that less space is taken up on a counter top. Motorized brush assembly 200 is held by a U shaped retaining bracket 16 and accessory brush head 10 is held by a second retaining bracket 17. In FIG. 2 we see a perspective view of the present invention in the use position. Water reservoir 2 has been filled with water by the user and has been placed on pump housing 30. Brush assembly 200 has been removed from cradle 16 and extendable hose 18 connects the pump housing 30 with the bottom of brush handle 8. Brush head assembly 400 is replaceably removable from handle 8 at break line 410. A pair of sheathed wires 22 leads from pump housing 30 to wall pack transformer 24. Brush tip 6 is caused to reciprocate when button 52 is pressed. Water 80 is pumped through hose 18 and exits at high velocity 81 out of the center of brush tip 4. FIG. 3 shows a side section view of the motorized brush assembly of the present invention. Hose 18 enters the bottom of handle 8. Two pairs of sheathed wires 46, 48 exit hose 18 via a watertight gasket 90. Wires 46 go to the switch 50 which activates the motor 83 that powers the water pump assembly 300. Wires 48 go to switch 52, which activates power to motor 32, which in turn powers reciprocating brush tip 6. Motor 32 powers gear train 56, which terminates in reciprocating shaft 40. Shaft 40 plugs into receptacle 60, which drives reciprocating shaft 42, located in brush head assembly 400. Shaft 42 is pivotally connected to pivot pin 43 which in turn is connected to oscillating brush tip 6. The center of brush tip 6 is stationary so that water, as it progresses up through tube 36 and out through right angle tube 14, is non-oscillating even when brush tip 6 is oscillating. Water 19 progresses up base 18 and into tube 36 and finally out tube 14 so that a strong, fine stream can be aimed at the gums and teeth of the user when switch 50 is pushed. FIG. 4 shows a side section view of the pump housing 30 and water reservoir 2 in the use position. Male fitting 21 mates with female fitting 20 in the water reservoir so that water 80 can flow down from the water reservoir 2 to the pump 86 and out through hose 18, which has an end coiled in compartment 70 as shown in FIG. 4. Batteries 72 allow the unit to be powered independently of a wall socket, however a wall pack transformer 24, shown in FIG. 2, allows the unit to be plugged into house voltage. Microprocessor chip 74 can play a song of two minutes in length thereby helping the user time his or her brushing activities. Sequentially blinking LED's, not shown, can also act as a timing device.

In the above described way, a person can brush their teeth using a motorized brush head and can also clean their gums with a fme stream of water all with one integrated, compact, economical unit. The placement of the water stream is such that a person can brush and clean their teeth and gums simultaneously.

Although the above drawings and description of drawings show a preferred embodiment of the present invention, it is to be understood that there may be other embodiments which would be obvious to one versed in the art of tooth and gum cleaning devices and which would be within the spirit and scope of the present invention.

What is claimed is:

1. A combination motorized tooth brush and gum cleaning device comprised of a fluid pump and pump housing, a water reservoir, a hollow toothbrush handle having within it a D.C. motor, a gear train assembly terminating in an oscillating shaft, a replaceable removable brush head assembly capable of fitting onto the top of said brush handle, said brush head assembly also containing a hollow tubular portion capable of carrying fluid to the center most portion of the bristle portion of the brush head, said brush handle connected to said pump housing by a hollow, flexible tube capable of carrying a fluid such as water from said pump to said brush handle and head assembly, said flexible tube also carrying two pairs of sheathed wires, one said pair connected from a power source located in said pump housing to a switch located in said brush handle for the purpose of turning on and off said D.C. motor, the other said pair of wires being connected from said power source to a second switch located in said handle for the purpose of turning on and off said pump.

2. A combination motorized toothbrush and gum cleaning device as claimed in claim 1 wherein said water reservoir is removable and replaceable and can nest with said pump housing when not in use.

3. A combination motorized toothbrush and gum cleaning device as claimed in claim 1 wherein said flexible hose stores out of sight in said pump housing.

4. A combination motorized toothbrush and gum cleaning device as claimed in claim 1 wherein said pump housing also contains a micro-processor chip and a speaker so that a melody lasting approximately two minutes in length can be played for timing purposes.

5. A combination motorized toothbrush and gum cleaning device as claimed in claim 1 wherein said water reservoir nests with said pump assembly and can be switched from a horizontal position to a vertical position for the purpose of taking up less counter space while in a storage position.

6. A toothbrush and gum cleaning device comprising:
a brush handle that has a top;
a brush head capable of fitting onto the top of the brush handle comprising:
a brush head body;
a brush on the brush head body, the brush having a plurality of bristles, and an outlet, positioned in a center portion of the brush bristles, for releasing a stream of fluid, the brush being capable of moving with respect to the brush head;
a hollow tubular portion capable of carrying fluid to the outlet;
a fluid pump;
a housing enclosing the pump therein;
a hollow flexible tube connecting the housing and the handle, wherein the tube is capable of carrying a fluid from the pump to the handle and the brush head;
wherein the brush handle further comprises a gear train assembly connected to a motor, terminating in a shaft and capable of moving the brush;
further comprising a means for supplying cower to the motor;
wherein the means for supplying power is a wire connection from a power source in the housing to the motor; and
wherein the flexible tube comprises two pairs of sheathed wires, one pair connected from a power source located in the housing to a switch located in the brush handle for the purpose of turning on and off the power supply means, the other pair of wires being connected from the power source to a second switch located in the handle for the purpose of turning on and off the pump.

7. A toothbrush and gum cleaning device comprising:
a brush handle that has a top;
a brush head capable of fitting onto the top of the brush handle comprising:
a brush head body;
a brush on the brush head body, the brush having a plurality of bristles, and an outlet, positioned in a center portion of the brush bristles, for releasing a stream of fluid, the brush being capable of moving with respect to the brush head;
a hollow tubular portion capable of carrying fluid to the outlet;
a fluid pump;
a housing enclosing the pump therein;
a hollow flexible tube connecting the housing and the handle, wherein the tube is capable of carrying a fluid from the pump to the handle and the brush head; and
further comprising a fluid reservoir that is removable and replaceable and can nest with the pump housing when not in use.

8. The toothbrush and gum cleaning device of claim 7 wherein the fluid reservoir is capable of being switched from a horizontal position to a vertical position for the purpose of taking up less counter space while in a storage position.

9. A toothbrush and gum cleaning device comprising:
a brush handle that has a top;
a brush head capable of fitting onto the top of the brush handle comprising:
a brush head body;
a brush on the brush head body, the brush having a plurality of bristles, and an outlet, positioned in a center portion of the brush bristles, for releasing a stream of fluid, the brush being capable of moving with respect to the brush head;
a hollow tubular portion capable of carrying fluid to the outlet;
a fluid pump;
a housing enclosing the pump therein;
a hollow flexible tube connecting the housing and the handle, wherein the tube is caoable of carrying a fluid from the pump to the handle and the brush head; and
wherein the housing further comprises a timer capable of informing the user as to the length of time of use of the cleaning device, the timer comprising a speaker and a micro-processor.

10. The combination motorized toothbrush and gum cleaning device comprising:
- a fluid pump;
- a pump housing;
- a fluid reservoir;
- a toothbrush handle;
- a gear train assembly driven by a motor and terminating in an oscillating shaft;
- a replaceable removable brush head assembly capable of fitting on top of the handle;
- a hollow flexible tube connecting the pump housing and the handle, and capable of carrying a fluid from the pump to the handle and head assembly;
- wherein the brush head assembly comprises a hollow tubular portion capable of carrying fluid to a center most portion of a bristle portion of the brush head; and
- wherein the pump housing comprises a micro-processor chip and a speaker capable of playing a melody lasting approximately two minutes in length for timing purposes.

* * * * *

UNITED STATES PATENT AND TRADEMARK OFFICE
CERTIFICATE OF CORRECTION

PATENT NO.     : 6,233,773 B1
DATED          : May 22, 2001
INVENTOR(S)    : Hans J. Karge and Robert C. Wood It is certified that error appears in the above-identified patent and that said Letters Patent is hereby corrected as shown below:

Title page,
Item [56], References Cited, U.S. PATENT DOCUMENTS, replace "4,619,009 10/1986 Rosenstater . . . 15/29" with -- 4,619,009 10/1986 Rosenstatter . . . 15/29 --.

Column 4,
Line 9, replace "cower" with -- power --.
Line 62, replace "caoable" with -- capable --.
Line 67, replace "micro-processor" with -- microprocessor --.

Signed and Sealed this

Eighteenth Day of March, 2003

JAMES E. ROGAN
*Director of the United States Patent and Trademark Office*